United States Patent [19]
Roth et al.

[11] Patent Number: 5,692,901
[45] Date of Patent: Dec. 2, 1997

[54] DISPOSABLE ADJUSTABLE FLOW PROPHY ANGLE (DAFPA)

[76] Inventors: Noah M. Roth, 1049 E. Cabana Cir. #1, Memphis, Tenn. 38107; James Cohen, 3337 Kirby Pkwy., Memphis, Tenn. 38115

[21] Appl. No.: 655,230

[22] Filed: Jun. 5, 1996

[51] Int. Cl.$^6$ ............................................. A61C 1/10
[52] U.S. Cl. .............................. 433/85; 433/82; 433/125
[58] Field of Search ............................ 433/80, 82, 83, 433/84, 85, 89, 125

[56] References Cited

U.S. PATENT DOCUMENTS

| | | | |
|---|---|---|---|
| 2,400,912 | 5/1946 | Britt et al. | 433/125 |
| 3,389,468 | 6/1968 | Lewis et al. | 433/82 |
| 3,691,636 | 9/1972 | Deuschle | 433/82 |
| 3,775,849 | 12/1973 | Condon | 433/125 |
| 3,826,004 | 7/1974 | Graceffo | 433/85 |
| 4,266,933 | 5/1981 | Warden et al. | 433/82 |
| 4,604,058 | 8/1986 | Fisher et al. | 433/125 |
| 5,022,857 | 6/1991 | Matsutani et al. | 433/85 |
| 5,062,796 | 11/1991 | Rosenberg | 433/82 |
| 5,069,620 | 12/1991 | Matsutani et al. | 433/82 |
| 5,352,118 | 10/1994 | Franetzki et al. | 433/82 |

*Primary Examiner*—Gene Mancene
*Assistant Examiner*—Ralph A. Lewis

[57] ABSTRACT

The device presented herein is a Disposable Adjustable Flow Prophy Angle (DAFPA) attachment with an integral feed mechanism to expel a predetermined quantity of abrasive medium into a polish cup. During use, the high speed rotation of the drive shaft driving the angled attachment will propel the abrasive medium into the flow channel, via a propellant screw. A sealing ring is incorporated to protect against any backflow of the abrasive medium. A significant feature of the device is the ability to continually adjust the flow of abrasive medium deposited into the polish cup by a calibrated flow adjustment knob, providing the advantage of selecting a predetermined flow rate, to accommodate the needs of the health care professional. The current procedure is more time consuming and less sanitary. In the proposed system the abrasive medium is fed continuously or on demand from an internal reservoir. The invention would apply to both disposable and metallic right angle units. The unit will be delivered with a charge of abrasive medium sufficient for a single use. The self contained device described herein will be more convenient, sanitary, and provide a financial savings from reduced shipping cost and waste disposal. The abrasive medium and prophy angle will be packaged, shipped, used, and disposed of in a single self contained unit. It should be noted that the embodiment shown and described herein is not inclusive of the invention and is simply one embodiment used for descriptive purposes.

8 Claims, 2 Drawing Sheets

5,692,901

DISPOSABLE ADJUSTABLE FLOW PROPHY ANGLE (DAFPA)

BACKGROUND OF THE INVENTION

The present invention relates to a disposable adjustable flow prophy angle. Currently there is no device in the dental industry that make use of the technology presented herein. Present systems are sold as two products—a disposable prophy angle and a small allotment of abrasive medium as separate units. The abrasive medium is spread over the orifice of the polish cup and used within the oral cavity. Many times during the procedure the dental professional is required to stop and refill the polish cup with the abrasive medium. This is not only time consuming and frustrating to the dental professional but it is unsanitary. During the procedure the abrasive medium is left open to the atmosphere, providing an opportunity for foreign products (i.e., viruses, bacteria, and other biological toxins) to entire the oral cavity. This becomes an even greater issue when taking into account the amount of damage done to surrounding tissue during a routine cleaning, leaving the patient more vulnerable to a possible infection. Therefore, there has been a need for a product that would allow dental professional to do the required procedure in an efficient manner while reducing risk to the patient. The proposed design will address these issues and more. The invention is applicable to both the disposable and the traditional metallic right angle units. In the first, the right angle units will be sterilized and pre-packaged for single use. The unit will come complete with a charge of abrasive medium sufficient for one use. The abrasive medium will be contained within reservoir the unit. In addition, the technology contained herein will provide means to repeatedly and accurately adjust the flow rate of abrasive medium deposited into the polish cup. This will not only eliminate the frustrating and time consuming act of having to manually refill the polish cup with abrasive medium, many time during the procedure, but will ultimately remove the risk incurred by leaving the abrasive medium exposed to the atmosphere. The self containment feature of the device provides an added benefit of reducing waste disposal cost. Presently there are four items of waste material for disposal; 1) abrasive medium container with unused medium, 2) accompanying packaging, 3) prophy angle 4) prophy angle packaging. The design presented herein will reduce waste disposal, subsequently reducing the disposal cost.

SUMMARY OF THE INVENTION

The Disposable Adjustable Flow Prophy Angle attachment provided with an integral feed mechanism to expel a charge of abrasive medium into a polish cup in an adjustable manner.

Consisting of:

Means to attach the prophy angle to a standard dental handpiece. Making use of the mechanical rotation to drive the propellant screw assembly. This assembly incorporates the main drive shaft of the device. The resulting force created by the handpiece will be sufficient to propel the abrasive medium into a flow channel and subsequently deposited into a polish cup for use in the oral cavity. A reservoir of abrasive medium sufficient for one cleaning is contained within the prophy angle. In addition, a sealing ring is incorporated into the design to protect against any backflow of the abrasive medium into the dental handpiece. A polish cup will serve as both the location where the abrasive medium will be deposited, and a means to lather the medium within the oral cavity. The rotary motion of the polish cup is accomplished by meshing two gears one attached to the main drive shaft and the other to the polish cup. The meshing of these gears adjust the angle of motion 90° from the center line of the main drive shaft, in a clockwise rotation. A significant feature of DAFPA in the ability to not only adjust the flow rate of abrasive medium but to do this repeatable, depending on the needs of the dental professional. The ability to adjust the flow rate of abrasive medium is accomplished by flow obstruction within the flow channel. The level of the flow obstruction device, and subsequently the flow rate, is accomplished by an adjustable knob which turns in a clockwise or counterclockwise fashion, increasing or decreasing the flow rate respectively. The varying flow rates will be calibrated for providing the dental professional with a scale on which to base the setting (i.e., a scale of 1–10, with 1 being the lowest flow rate and 10 the greatest). Such a scale will provide for the repeatability of a desired flow rate from use to use. Repeatability is a significant feature of the current design, particularly advantageous to a device that is intended to be used by a diverse group individuals. In an alternate embodiment of this invention, the abrasive medium will flow into the polish cup on demand. It should be noted with great emphasis that the embodiment shown and described herein is not inclusive of the invention and is simply one embodiment used for illustrative purposes.

DETAILED DESCRIPTION OF THE DRAWINGS-PREFERRED EMBODIMENT

Figure 1:
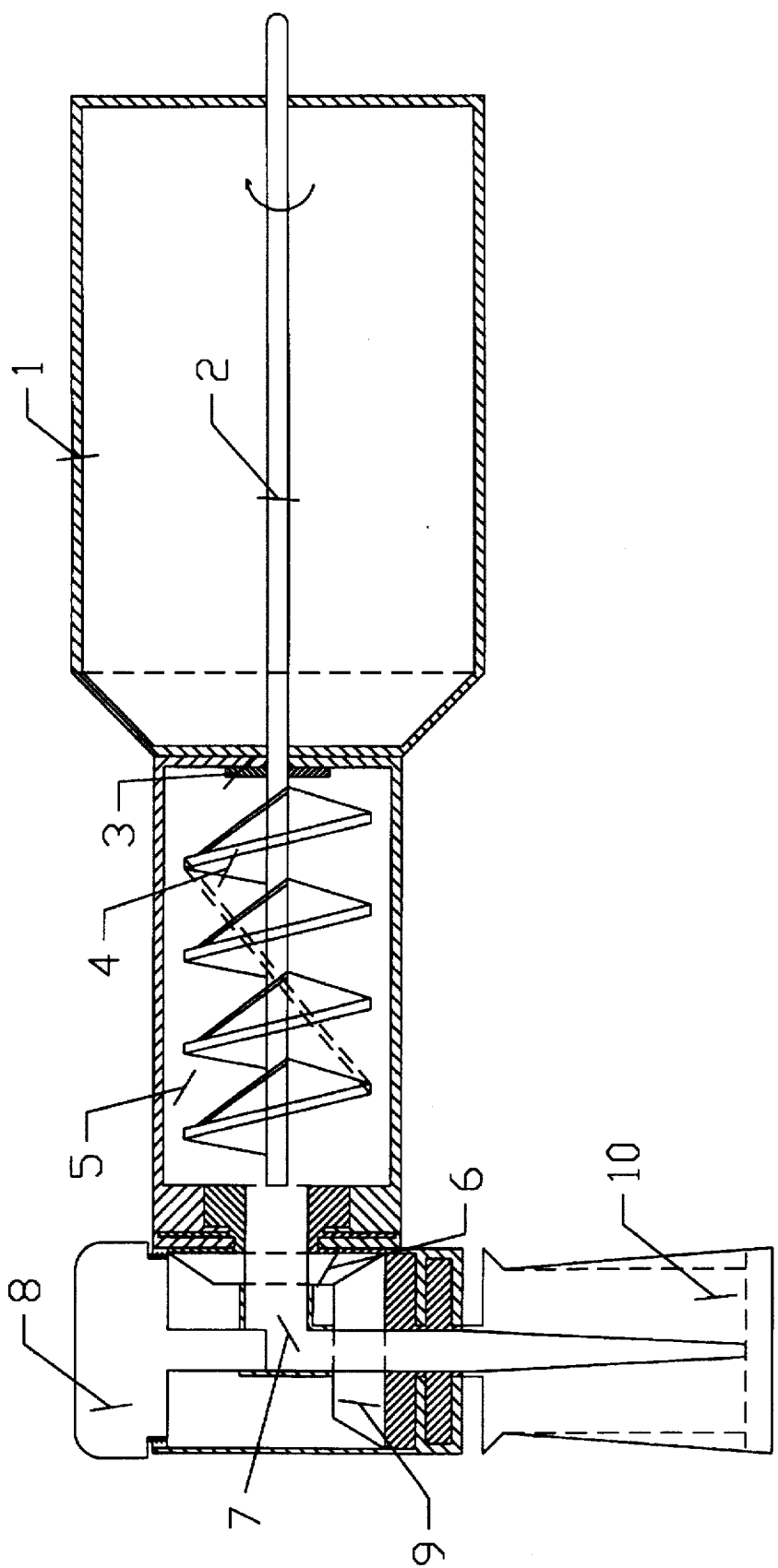
FIG. 1 A longitudinal sectional view taken through the Disposable Adjustable Flow Angle. Showing the mechanisms intrinsic to its use.
Figure 2:
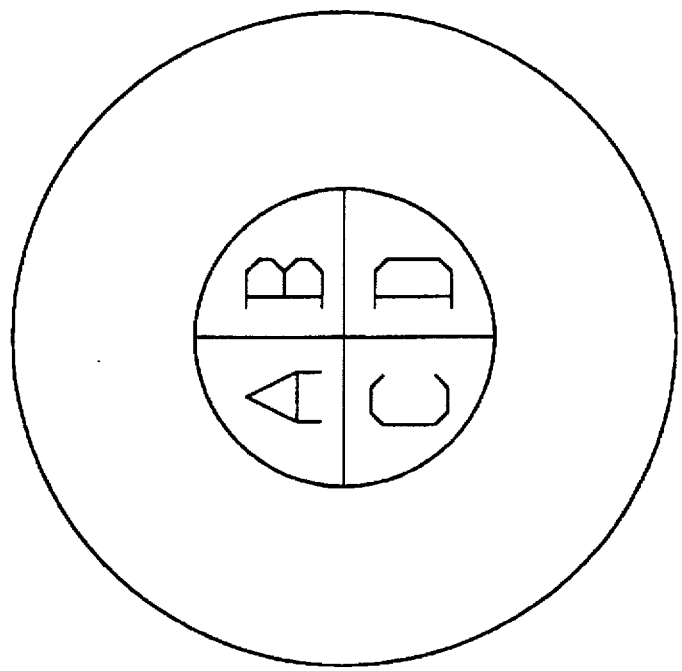
FIG. 2 A fragmented view showing a side and top profile of a gear typical of that found in Drive Gear (6) and Driven Gear (9).
Figure 2:
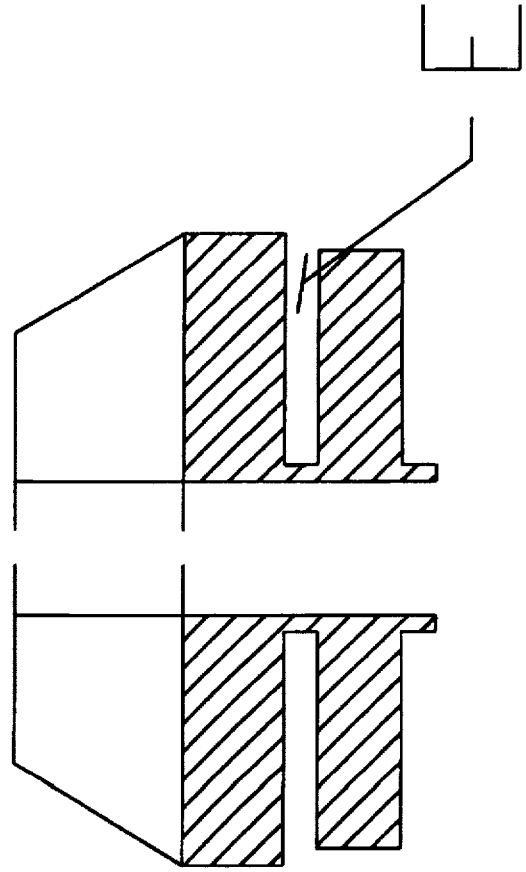

A Disposable Adjustable Flow Prophy Angle in accordance with the present invention as described herein by FIG. 1 and FIG. 2, part numbers: 1–10, identification letters: A–E. Unless otherwise stated all numbers refer to those of FIG. 1, when additional figures are referenced they will be specified.

The housing (1) forms the exterior geometry of the prophy angle. In addition, the housing (1) also provides the support and structure for all internal workings. Of significance is the flow channel formed by the housing (1). The geometric structure of the housing (1) is similar in dimension to that of current devices. This geometric structure of the housing (1) is one that is currently excepted by the dental community.

Positioned within the housing (1) is the drive shaft assembly (2). Drive shaft assembly (2) attaches to a dental handpiece of the type wherein the drive shaft assembly (2) is driven by some mechanical means (i.e., electric, air, etc.). The drive shaft (2) provides the motion and subsequent force necessary to the workings of the device.

Located at the transition from the external to the internal environment of the housing is a sealing ring (3). Sealing ring (3) provides protection against backflow of the abrasive medium. If the abrasive medium were to flow into the dental handpiece it would become damaged and result in excessive repair cost.

Moving distally through the housing (1) the drive shaft assembly (2) incorporates a propellant screw (4). Propellant screw (4) will be driven by the dental handpiece via the drive shaft (2). Rotation of the propellant screw in this manner will provide force sufficient to expel the charge of abrasive medium from its reservoir (5) into the flow channel (7) and subsequently into the polish cup (10). Dimensions of the propellant screw (4) will be consistent with the that required to expel the abrasive medium into the polish cup (10). There will be sufficient leakage in the housing (1) to insure against a vacuum being formed within the reservoir (5).

At the most distal end of the drive shaft (2) is drive gear (6) which meshes at a 90° angle with driven gear (9), the latter attached to the polish cup (10), providing rotary motion to the polish cup (10) at an angle of 90° relative to the axis of rotation of the drive shaft (2). Drive gear (6) and driven gear (9) are of similar construction to allow for the passage of the abrasive medium through the device. FIG. 2 shows a top view of the gear described wherein channels (A), (B), (C), (D) provide a path by which the abrasive medium may be discharged from the medium reservoir (5), into the flow channel (7), and into the polish cup (10) were it will be used within the oral cavity. FIG. 3 illustrates a mechanism by which drive gear (6) and driven gear (9) are secured within the housing (1), this is accomplished by support grove (E). This insures not only constant mesh of the two gears but adds to the stability and overall robustness of the design.

Flow channel (7) is a permanent feature of the housing (1), constructed by injection molding or a similar process. Obstructing the flow channel (7) is a flow adjustment knob (8) used to control the flow rate of abrasive medium expelled into the polish cup (10). Flow adjustment knob (8) will change the flow rate by obstructing the flow channel (7). Turning of flow adjustment knob (8) in either a clockwise or counterclockwise motion will decrease or increase the flow rate of abrasive medium, respectively. Flow adjustment knob (8) will be calibrated with setting from 1-10, with 1 the lowest setting and 10 being the greatest. Such a scale will provide for the repeatability of a desired flow rate from use to use. Repeatability is a significant feature of the current design, particularly advantageous to a device that is intended to be used by a diverse group individuals. It should be noted that the mechanism by which the flow rate is changed is not crucial to the technology. It is the underlying ability of being able to adjust the flow rate that is of significance.

In the embodiment shown a set of matching threads between the flow adjustment knob (8) and the housing (1) accomplishes the task of allowing the level of flow obstruction to be changed. The distal end of the polish cup (10) contains an opening sufficient to allow desired amounts of abrasive medium to be expelled at both the minimum and maximum flow rates. Once the abrasive medium has been deposited within the polish cup (10) it will be used within the oral cavity.

In accordance with the present invention a reservoir of abrasive medium (5) is supplied, sufficient for one use, contained within the housing (1) of the disposable adjustable flow prophy angle. The device is totally self contained removing the need for additional containers or conduits.

Although the present invention has been described in connection with the embodiment shown it does not exclude any additions, modifications, substitutions or deletions made which lie within the scope of the appended claims.

What is claimed is:

1. A Disposable Adjustable Flow Prophy Angle comprising:

an elongated housing having a proximal end for connection to a dental handpiece and a distal end connected to a polishing cup, said housing including a hollow section forming a reservoir suitable for holding a medium, said polishing cup having an open first end for receiving a tooth to be polished and a second end rotatably mounted to said distal end of the elongated housing, said polishing cup second end having an opening for receiving a medium, a medium flow channel extending from said reservoir to said opening in the polishing cup second end, a rotatable drive shaft extending through said elongated housing having proximal and distal ends, the drive shaft proximal end adapted for connection to a dental handpiece and the drive shaft distal end being connected to a gear mechanism for rotating said polishing cup when the drive shaft is rotated, said drive shaft extending through said reservoir and having a screw mounted thereto for forcing medium from said reservoir through the medium flow channel to said polishing cup when said drive shaft is rotated, and an adjustable flow obstruction element connected to said flow channel for controlling the flow rate of medium from the reservoir to the polishing cup.

2. A Disposable Adjustable Flow Prophy Angle according to claim 1, in combination with a dental handpiece wherein said housing proximal end and said drive shaft proximal end are attached to said dental handpiece and rotation of the drive shaft is supplied by mechanical means.

3. A Disposable Adjustable Flow Prophy Angle according to claim 1, further including a seal between said reservoir and said rotatable drive shaft to insure against any backflow of the medium into the handpiece.

4. A Disposable Adjustable Flow Prophy Angle according to claim 1, wherein said gear mechanism changes the direction of motion 90° relative to the drive shaft center line for the purpose of supplying rotary motion to the polish cup.

5. A Disposable Adjustable Flow Prophy Angle according to claim 4, wherein said flow channel has a bend between said reservoir and said polishing cup and said adjustable flow obstruction element includes a portion which extends into said flow channel bend for obstructing the flow of medium and an adjustment knob connected to said portion for adjusting the amount obstruction caused by said portion thereby allowing for the flow of medium to be adjusted.

6. A Disposable Adjustable Flow Prophy Angle according to claim 1, wherein said adjustable flow obstruction element includes a portion which extends into said flow channel for obstructing the flow of medium and an adjustment knob connected to said portion for adjusting the amount obstruction caused by said portion thereby allowing for the flow of medium to be adjusted.

7. A Disposable Adjustable Flow Prophy Angle according to claim 1, wherein the adjustable flow obstruction element includes a scale calibrated for repeatable flow rates of medium.

8. A method of using the Disposable Adjustable Flow Prophy Angle of claim 1, wherein an abrasive polishing medium is delivered to a patient's tooth by placing the abrasive medium in said reservoir, rotating said screw to force the abrasive medium through said flow channel to said polishing cup and placing the polishing cup over the patient's tooth.

* * * * *